(12) United States Patent
Smith et al.

(10) Patent No.: US 6,987,232 B2
(45) Date of Patent: Jan. 17, 2006

(54) SENSOR AND METHOD FOR DETECTING A PATIENT'S MOVEMENT VIA POSITION AND OCCLUSION

(75) Inventors: Toby E. Smith, Broken Arrow, OK (US); Craig L. Cooper, Inola, OK (US)

(73) Assignee: Bed-Check Corporation, Tulsa, OK (US)

( * ) Notice: Subject to any disclaimer, the term of this patent is extended or adjusted under 35 U.S.C. 154(b) by 122 days.

(21) Appl. No.: 10/776,959

(22) Filed: Feb. 11, 2004

(65) Prior Publication Data

US 2005/0011738 A1    Jan. 20, 2005

Related U.S. Application Data

(60) Provisional application No. 60/487,021, filed on Jul. 14, 2003.

(51) Int. Cl.
*H01H 35/36* (2006.01)
(52) U.S. Cl. .................. 200/85 R; 200/85 A; 200/511; 340/573.5; 600/300; 338/99
(58) Field of Classification Search ............. 200/85 R, 200/85 A, 86 R, 511, 329; 340/573.1–573.5, 340/529, 688; 338/47, 99; 600/300
See application file for complete search history.

(56) References Cited

U.S. PATENT DOCUMENTS

| 4,446,345 | A | * | 5/1984 | Sheiry ...................... 200/85 R |
| 5,142,109 | A | * | 8/1992 | O'Meara et al. .......... 200/86 R |
| 5,353,012 | A | | 10/1994 | Barham et al. |
| 5,659,905 | A | * | 8/1997 | Palmer et al. ................ 5/88.1 |
| 5,808,552 | A | * | 9/1998 | Wiley et al. ............. 340/573.4 |
| 6,013,882 | A | * | 1/2000 | Boetzkes .................... 200/86.5 |
| 6,281,455 | B1 | * | 8/2001 | Plottnik et al. ........... 200/61.44 |
| 6,307,476 | B1 | * | 10/2001 | Smith et al. .............. 340/573.1 |
| 6,417,777 | B2 | * | 7/2002 | Fitzgerald et al. .......... 340/687 |
| 6,696,653 | B1 | * | 2/2004 | Smith et al. .............. 200/85 R |
| 2003/0216670 | A1 | | 11/2003 | Beggs |

* cited by examiner

*Primary Examiner*—K. Lee
(74) *Attorney, Agent, or Firm*—Terry L. Watt; Fellers, Snider, Blankenship, Bailey & Tippens, P.C.

(57) ABSTRACT

There is provided herein a sensor for use in connection with an electronic patient monitor, wherein the sensor preferably uses a linearly configured resistive ladder with spaced-apart resistors as a means of determining at least approximately a location of the patient on the sensor as well as an approximate length of the sensor which is compressed by the patient. By continuously determining both of these quantities over time it is possible to track the patient's movement and determine to what extent the patient needs to be manually turned and/or the extent to which a next-scheduled turn can be skipped.

44 Claims, 4 Drawing Sheets

SENSOR AND METHOD FOR DETECTING A PATIENT'S MOVEMENT VIA POSITION AND OCCLUSION

RELATED APPLICATION

This application claims the benefit of U.S. Provisional Patent Application Ser. No. 60/487,021 filed on Jul. 14, 2003.

FIELD OF THE INVENTION

This invention relates generally to monitoring systems and more particularly concerns devices and systems used to monitor seated or lying patients in homes or in medical environments such as hospitals, institutions, and other caregiving environments so as to reduce the risk that such patients will develop decubitus ulcers.

BACKGROUND OF THE INVENTION

It is well known that patients who are confined to a bed or chair for extended periods of time are at risk of developing decubitus ulcers, i.e., pressure sores, or bed sores as they are more commonly known. These ulcers are often seen to develop within soft tissue that is compressed between a bed or chair surface and a patient's weight-bearing bony prominences, the compressed tissue being at least partially of deprived of oxygenated blood flow. A continued lack of blood flow, and resultant lack of oxygen, can result in cell death, which may be evidenced in the form of pressure sores. Pressure sores do not develop immediately, but rather form over time, with the development speed depending on a number of factors including the firmness and friction of the supporting surface against the patient's skin, the patient/ambient temperature, the amount of moisture in contact with the skin, and the health and susceptibility of the skin due to age, illness, and/or nutrition.

One venerable and generally accepted means of reducing the risk of decubitus ulcer development in bedfast patients is to turn them regularly, usually at approximately two hour intervals. For example, a patient in a back rest position might be periodically rolled to one side or the other, such motion helping to maintain blood flow to soft tissue that is under compression. Similar strategies are employed for patients that are confined to a chair for long periods of time. Obviously, an assisted-movement strategy relies largely on the vigilance of the (often harried) attending staff to insure that the patient is properly relocated. Further, it is far too easy for the busy caregiver to let the time for turning the patient slip by in the press of other daily emergencies. To the extent that the caregiver is too busy or forgets to perform this service, this method can fail to achieve its purpose. Further, this sort of strategy can be counterproductive for use with the patient that has some capacity for self-movement when, for example, the patient may have turned himself just before the caregiver arrived to manually turn him, in which case the caregiver will likely place the patient back in the position from which he recently moved, thus inadvertently exacerbating the problem. Further, after being rolled to a new position the patient might return to the original "comfortable" position after the caregiver leaves which would obviously negate the effects of the reposition.

The process of moving a patient to another position is admittedly disruptive to the patient and this is especially true at night, since the patient—if he or she were sleeping—will be awakened for the purpose of relocation. The typical two-hour movement interval must be observed around the clock if the method is to be effective, so it is necessary to disturb the patient—who might be sleeping soundly at the time—to make the required adjustment in position. Further, this adjustment might not have even been necessary, or even counter indicated, if the patient had recently moved of his or her own volition. Thus, in many situations it would be advantageous for the caregiver to know if and when the patient last moved his or herself. Then, if the last movement were within a prescribed period of time, it might be possible to spare the patient an unnecessary interruption in his or her healing sleep. The caregiver would then relocate the sleeping patient, only if that relocation were actually required. Further, knowing which patients do not need to be moved could result in a substantial savings in labor costs, as the time that would otherwise be devoted to moving the patient that did not actually need to be moved could be productively applied elsewhere. That being said, as useful as this sort of information might be to the health care provider, however, the present state-of-the-art in patient management does not provide this sort information.

Generally speaking, there are two broad approaches to dealing with decubitus ulcers: mechanical and medicinal. The medical approach is concerned with the development of medicinal compounds and methods for treating the ulcer after it occurs. This approach is obviously quite useful but ultimately it is reactive, rather than proactive, because it attempts to minimize the damage occasioned by the ulcer after it has formed.

On the other hand, the mechanical approach typically utilizes a specialized mattress, pad, or other arrangement, which is designed to lessen the weight-pressure that is brought to bear on the patient's bony prominences. These devices might be either static (e.g., foam, air, or water mattresses) or dynamic (e.g., compartmentally inflatable mattresses that dynamically shift the locus of support pressure under the patient over time. Examples of inventions in the prior art that are generally concerned with this subject matter include U.S. Pat. Nos. 4,425,676, 5,926,884, and 5,072,468, the disclosures of which are incorporated herein by reference. Generally speaking, a mechanical approach is to be preferred because it seeks to spare the patient the discomfort and risk associated with bed sores and reduces the costs associated with treating such, which costs can potentially accrue to the facility under some circumstances.

One enhanced variant of the mechanical approach utilizes a proactive strategy that seeks to avoid tissue death by using a combination of automatic monitoring of the patient's movement together with notification of a caregiver if the patient's movement pattern does not meet or exceed some predetermined level. Upon receipt of such notice, the caregiver will then manually turn the patient, as has been the custom heretofore. This approach, if properly implemented, has the potential to dramatically reduce the risk of pressure sores while keeping the cost of such preventative measures within the reach of small institutions and individual patients.

It is this last approach, electronic patient monitoring combined with caregiver intervention, which has been adopted by the instant inventors. As such, general information relating to mat-type sensors and electronic monitors for use in patient monitoring is relevant to the instant disclosure and may be found in U.S. Pat. Nos. 4,179,692, 4,295,133, 4,700,180, 5,600,108, 5,633,627, 5,640,145, 5,654,694, and 6,111,509 (the last of which concerns electronic monitors generally). Additional information may be found in U.S. Pat. Nos. 4,484,043, 4,565,910, 5,554,835, 5,623,760, 6,417,777 (sensor patents) and U.S. Pat. No. 5,065,727 (holsters for electronic monitors), the disclosures of all of which patents are all incorporated herein by reference. Further, U.S. Pat. No. 6,307,476 (discussing a sensing device which contains a validation circuit incorporated therein), U.S. Pat. No. 6,544,200, (for automatically configured electronic monitor alarm parameters), and U.S. patent Ser. No. 09/878,088 (for a binary switch and a method of its manufacture), and Ser. No. 10/125,059 (for a lighted splash guard) are similarly incorporated herein by reference.

Additionally, sensors other than mat-type pressure sensing switches may be used in patient monitoring including, without limitation, temperature sensors, patient activity sensors, toilet seat sensors (see, e.g., U.S. Pat. No. 5,945,914), wetness sensors (e.g., U.S. Pat. No. 6,292,102), decubitus ulcer sensors (e.g., U.S. Pat. No. 6,646,556), etc., all of which are incorporated herein by reference. Thus, in the text that follows the terms "mat" or "patient sensor" should be interpreted in its broadest sense to apply to any sort of patient monitoring switch or device, whether the sensor is pressure sensitive or not.

Finally, pending U.S. patent application Ser. No. 10/397, 126, also incorporated herein by reference, discusses how white noise can be used in the context of decubitus ulcer prevention.

Heretofore, as is well known in the patient monitoring and, more particularly, the decubitus ulcer prevention arts, there has been a need for an invention to address and solve the above-described problems. Accordingly, it should now be recognized, as was recognized by the present inventors, that there exists, and has existed for some time, a very real need for a system for monitoring patients that would address and solve the above-described problems.

Before proceeding to a description of the present invention, however, it should be noted and remembered that the description of the invention which follows, together with the accompanying drawings, should not be construed as limiting the invention to the examples (or preferred embodiments) shown and described. This is so because those skilled in the art to which the invention pertains will be able to devise other forms of this invention within the ambit of the appended claims.

SUMMARY OF THE INVENTION

In accordance with a first aspect of the instant invention, there is provided a patient sensor and electronic monitor combination that continuously monitors a bedfast or chair bound patient to determine whether or not that patient's amount of movement is sufficient to, for example, eliminate the next scheduled turning by the caregiver.

In a first preferred arrangement of the instant invention, there is provided a sensor for use in connection with an electronic patient monitor, wherein the sensor uses a resistive ladder with spaced-apart resistors as a means of determining at least approximately a location of the patient on the sensor as well as an approximate length of the sensor which is contacted by the patient. By continuously determining both of these quantities over time it is possible to track the patient's movement and determine to what extent the patient needs to be manually turned and/or the extent to which a next-scheduled turn can be skipped. In one preferred embodiment, the resistors will be linearly spaced apart within the patient sensor.

According to another preferred arrangement, a plurality of resistive ladders arranged in a parallel configuration, one above the other, will be used to determine the position and contact region of a patient with these multiple sensors and, additionally, will be used to calculate some relative value of the shear which is being experienced by the patient as his or her body slides down in the bed. Preferably, the resistive elements will be linearly spaced apart.

The foregoing has outlined in broad terms the more important features of the invention disclosed herein so that the detailed description that follows may be more clearly understood, and so that the contribution of the instant inventor to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Further, the disclosure that follows is intended to apply to all alternatives, modifications and equivalents as may be included within the spirit and scope of the invention as defined by the appended claims. Finally, it should be understood that the phraseology and terminology employed herein are for the purpose of description and should not be regarded as limiting, unless the specification specifically so limits the invention.

While the instant invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

BRIEF DESCRIPTION OF THE DRAWINGS

Other objects and advantages of the invention will become apparent upon reading the following detailed description and upon reference to the drawings in which.

DETAILED DESCRIPTION OF THE INVENTION

According to a preferred aspect of the instant invention, there is provided an electronic patient monitor for use with a patient sensor, wherein the attached sensor is at least suitable for determining the location of the patient in the bed or chair through the use of a resistive ladder.

General Environment of the Invention

Figure 1:
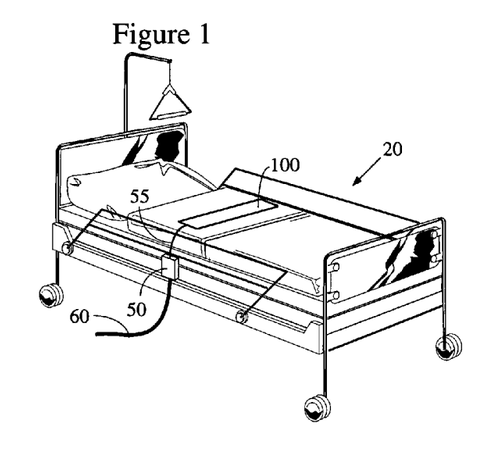
FIG. 1 illustrates the general environment of the instant invention, wherein an electronic patient monitor is connected to a bed mat.

Generally speaking, electronic patient monitors of the sort discussed herein work by first sensing an initial status of a patient, and then generating a signal when that status changes (e.g., the patient changes position in the bed, the patient fails to change position in the bed, the patient leaves the bed, the sensor changes from dry to wet, the temperature of the sensor changes, etc.) or, in some cases, if the initial condition persists for too long a period of time (e.g., if the patient has not moved during a predetermined time interval). Turning now to FIG. 1 wherein the general environment of one specific embodiment of the instant invention is illustrated, in a typical arrangement a pressure sensitive mat 100 sensor is placed on a bed 20 where it will lie beneath a weight-bearing portion of the reclining patient's body, usually the buttocks and/or shoulders. Generally speaking, the mat 100/electronic monitor 50 combination works as follows. When a patient is placed atop the mat 100, the patient's weight compresses it, thereby closing an internal electrical circuit. This circuit closure is sensed by the attached electronic patient monitor 50 and, depending on its design, this closure may signal the monitor 50 to begin monitoring the patient via the mat 100. Additionally, in some embodiments, the monitoring phase is initiated by a manually engaged switch. Thereafter, when the patient's status changes (e.g., if weight is removed from the sensing mat 100, thereby breaking the electrical circuit, or if the patient changes position on the mat 100) this change is sensed by the attached electronic patient monitor 50 which responds to the changing condition according to its internal design and/or programming.

In some configurations, the changed circumstance of the patient will result in a signal or alarm being sent to notify a caregiver of the event. For example, if the patient has risen to his or her feet and left the bed, an electronic signal will be sent to a remote nurses/caregivers station via electronic communications line 60. In other arrangements, and more pertinent to the instant disclosure, if the patient's circumstance does not change for some period of time (e.g., if the patient has remained motionless within the bed or chair) an alarm will be sounded. In still other arrangements, an alarm might be sounded if, for example, the patient's skin temperature rises, which can in some instances be a precursor to the formation of a decubitus ulcer. Note that additional electronic connections not pictured in this figure might include a monitor power cord to provide a source of AC power although, as generally pictured in this figure, the monitor 50 can certainly be configured to be either battery or AC powered. In other configurations, if the monitor 50 is designed to track the patient's position in the bed, a change in position would not necessarily result in an alarm being generated, but rather such a change might be recorded by the monitor 50 for later review and analysis by the staff or for purposes of monitoring the patient's movement history as is discussed at greater length hereinafter. Similarly, if the patient has not moved for some predetermined period of time, that circumstance could also generate an alarm. Those of ordinary skill in the art will recognize that the previous examples are just a few of the many variations of this general scheme that are possible.

Figure 2:
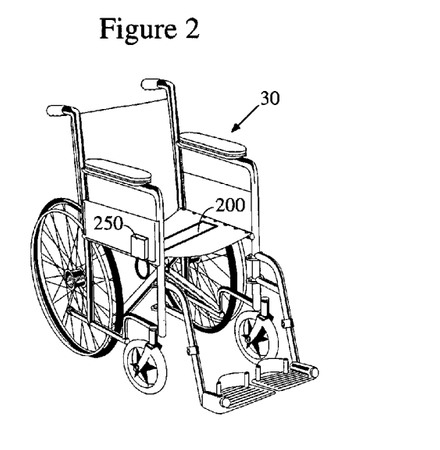
FIG. 2 illustrates the general environment of the instant invention, wherein an electronic patient monitor is connected to a chair mat.

In another common arrangement, and as is illustrated in FIG. 2, a pressure sensitive chair sensor 200 might be placed in the seat of a wheel chair or the like for purposes of monitoring a patient seated therein. As has been described previously, a typical configuration utilizes a pressure sensitive mat 200 that is connected to an electronic chair monitor 250 that is suspended from the chair 30. Because it is anticipated that the patient so monitored might choose to be at least somewhat mobile, the monitor 250 will usually be battery powered and will signal a patient change event (or, patient non-change event) via an internal speaker, rather than a hardwired nurse-call. Of course, those of ordinary skill in the art will understand that in some instances the monitor 250 can be configured to communicate wirelessly with the nurses' station through RF, IR, ultrasonic or other communications technology.

Preferred Embodiments

Figure 3A:
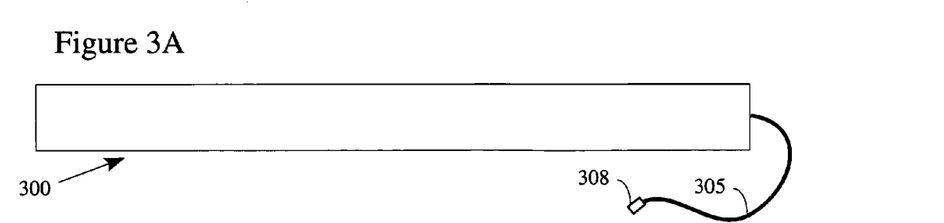
FIG. 3 contains an illustration of the main features of a preferred embodiment of the instant pressure sensitive mat.

In accordance with a first aspect of the instant invention and as is generally shown in FIG. 3A, there is provided a patient sensor 300 which is designed to determine at least an approximate longitudinal position of the patient on the sensor and, additionally, to determine an occluded length of the sensor.

Figure 3B:
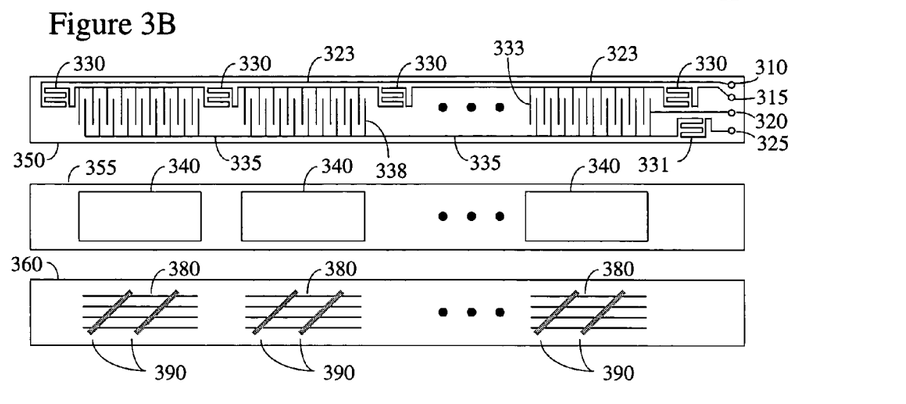

In a first preferred arrangement, a mat-type sensor with a resistive (or similar component) ladder which is comprised of a plurality of resistive elements arrayed in a spaced apart configuration is used to determinate at least a longitudinal position of the patient on the sensor. As is illustrated in FIG. 3B, the preferred mat 300 is comprised of three layers: upper 350 and lower 360 non-conductive layers, and inner spacer 355 which is positioned between and separates the upper 350 and lower 360 layers.

In a preferred arrangement, the pressure sensitive mat of the instant invention is generally rectangular in shape and provides external electrical connectivity by way of electrical line 305 and connector 308. Preferably the connector 308 will take the form of an RJ-11 or similar connector. As is best illustrated in FIG. 3B, the preferred sensor 300 is comprised of a "sandwich" of three layers: two outer nonconductive layers 350 and 360, and, preferably, an inner nonconductive central spacer 355. In the preferred embodiment, each of these layers is made of a flexible material such as polyester. Additionally, it has been contemplated by the inventors that polyethylene layers might be bonded to each of these of the components 350, 355, and 360 to make it possible to fuse them together as a single unit by, for example, heat sealing, or, alternatively, by pressure sensitive adhesive.

Preferably, the inner surface of upper member 350 will contain a screened or printed pattern of electrically conductive material such as silver-based ink or, alternatively, carbon ink black, etc., which renders portions of that surface electrically conductive. In a preferred arrangement, the screened material is laid onto the inner surface of upper member 350 in such a way that at least two different electrically isolated circuits are created. In FIG. 3B, a first circuit 335 is created which is preferably accessible via either connector 320 or 325. Preferably, contact circuit 335 will contain a plurality of cross members 338 which are interleaved with the corresponding cross members 333 from circuit 323. As can be seen, one preferred optional feature of this circuit is that it by measuring the resistance from connector 320 to connector 325 it is possible to determine the actual value of the single resistive element 331 (i.e., to determine the actual resistance of the "calibration resistor"). In a preferred embodiment, the calibration resistive element 331 will be sized to have the same value as the sensing elements 330, although those of ordinary skill in the art will recognize that this is not essential. A principal reason for including such a separate resistive element circuit is that it permits the instant invention to accommodate manufacturing variations that might occur in printing the conductive portions of the mat 300. That is, in the preferred arrangement the resistive elements 330 and 331 will formed of conductive ink and will be printed onto the nonconductive layer 350. Although this method of creating the circuits 323 and 335 is very cost effective, batch variations in ink thickness, conductivity, etc., can cause each of the resistive elements to be different in value than was called for in the specification. Obviously, to the extent that this variation is relatively large and not otherwise accounted for, the determination of the patient's position on the sensor could be made unreliable. One method of potentially reducing this inaccuracy is by individually recalibrating each of the resistors each time the mat is used (e.g., by having the caregiver successively individually activate each of the switches 410 through 470) at the direction of the CPU. A more efficient alternative, however, is to separately measure the resistive value of calibration element 331, and provided that any manufacturing variation that might be present in resistive elements 330 is comparably present in calibration element 331, modify the calculations that are described hereinafter according to methods well known to those of ordinary skill in the art to account for less than perfect manufacturing. For example, if the resistance of the calibration element 331 is expected to be 100 ohms, and the actual measurement gives 90 ohms, then it is straightforward to adjust the calculations that produce the patient's location to reflect this variation (e.g., by simply scaling all measured resistances by the factor 100/90). Finally, note that another way of calibrating the preferred resistive ladder is by putting a constant current into connector 310 while no patient is present and reading the resulting voltage at 310 while grounding 315. Assuming for purposes of illustration that all of the resistive elements 330 have the same nominal value, this reading will make it possible to determine the total number of resistors in the system, as well as the actual total resistivity. To the extent the measured resistivity differs from the nominal resistivity, subsequent readings can be adjusted proportionally.

Circuit 333 is preferably accessible by both connector 310 and connector 315. As was mentioned previously, this circuit preferably has a plurality of cross members 333 which are interleaved with, but electrically isolated from, cross members 338 of contact circuit 335. Additionally, circuit 333 contains a plurality of identical resistive elements 330 which are connected in series. By measuring the resistance across connectors 310 and 315 it is possible to measure the total resistance in the circuit 333.

Central spacer 355 is preferably made of a flexible and resilient material such as polyester and contains a plurality of apertures 340 therethrough. The location of each aperture 340 should at least approximately coincide with the interleaved cross members 333 and 338 when the surfaces 350, 355, and 360 are assembled into the single sensor 300.

Upper member 360 preferably contains a plurality of conductive elements 380, which at least partially span the apertures 340. In the preferred embodiment, conductive elements 380 are configured such that when weight is placed on the mat 300, that pressure will force the conductive elements 380 through one or more apertures 340 and into contact with circuits 323 and 335. More particularly, conductive elements 380 are configured such that when they come into contact with cross members 333 and 338 they cause an electrical short between discrete circuits 323 and 335. Further, and is explained in more detail below, based on the measured resistances across connectors 310, 315, 320, and/or 325 it is possible to reconstruct the location of the patient on the mat, as well as the proportion of the mat 300 which is compressed (or, more generally, occluded) by the patient, the latter measure being indicative of the orientation of the patient on the mat 300. Additionally, non-conductive support elements 390 are preferably superimposed upon the conductive elements 380 to help prevent inadvertent contact between the conductive elements 380 and the cross members 333 and 338 through the apertures 340 when there is no patient on the mat 300.

In the preferred embodiment, circuits 323 and 335 are laid onto their respective non-conductive surfaces 350 and 360 by printing with a flexible conductive ink such as silver-based ink. Additionally, it is preferable for purposes of manufacturing efficiency that resistive elements 330 be formed of the same ink or other conductive material as is used to create the circuits 323 and 335. As those of ordinary skill in the art will understand, resistive elements 330 can readily be formed to match a desired resistive value by simply adding length to the path traveled by electricity in completing the circuit. Because the conductive material has an inherent resistance, adding length to the path correspondingly increases the resistance of the circuit. As a consequence, in the preferred embodiment the resistive elements 330 are formed by printing additional lengths of the same conductive material used elsewhere in circuits 323 and 335. One obvious advantage of this approach is that it is more cost effective to print all of the elements of the mat in a single pass. Additionally, if a discrete resistor were to be used that element could very well introduce a hard bump or bulge in the mat surface, which might prove to be uncomfortable for the patient resting thereon. That being said, those of ordinary skill in the art will recognize that there are many ways that resistive or other elements suitable for use with the instant invention could be introduced into the circuits 323 and 335.

Figure 4:
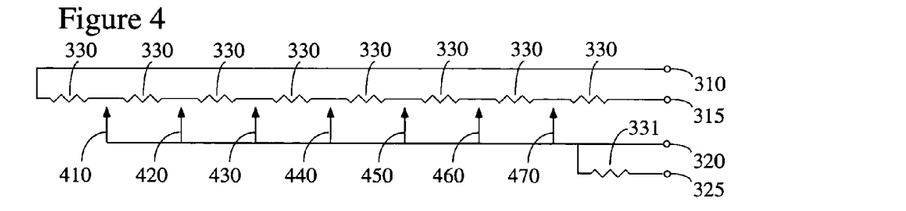
FIG. 4 is an electronic schematic of the preferred pressure sensitive mat of FIG. 3.

Turning now to FIG. 4, this figure contains a schematic illustration of a preferred embodiment of the circuits of FIG. 3. As can be seen, the closure of switches 410, 420, 430, 440, 450, 460 and/or 470 engage different numbers of resistive elements 330. This arrangement allows the attached electronic monitor to determine at least approximately the position of the patient on the sensor 300 and the number of switches (410 to 460) that have been closed by the patient's weight, this latter count being representative of the patient's position on the mat.

According to a preferred arrangement, given the circuit configuration of FIG. 4, it is possible to determine the position and orientation of the patient on the mat according to the following preferred scheme. First, as an initial calibrating measurement and as has been described previously, it is preferred that the resistance between connectors 325 and 320 be measured and, assuming that any significant variation in ink quality or quantity has affected every resistive element 330 in the same general fashion, this measurement can be used to determine the approximate resistance of a single resistive element in the circuit which then provides a correction factor that can be applied in subsequent calculations.

Continuing with the discussion of FIG. 4, note that by measuring the resistance (or alternatively the voltage or any other similar quantity) between leads 315 and 320 an estimate of the patient's position on the mat may be determined (circuit "C1" hereinafter). More specifically, the measured resistance will be indicative of the nearest switch (410 through 460) to the connector-end that is engaged. By way of example, and assuming for purposes of illustration only that each resistive element 330 is the same value, if contacts 440 and 450 are both engaged, the measured resistance between 315 and 320 will be approximately three times the resistance of individual resistor 330. Obviously, the calculated resistive value across these contacts will vary depending on the precise combination of contacts that are engaged and the values of the resistances. Further, it is readily possible to build a table or develop an equation that relates the measured resistance to every possible position of the patient on the mat 300. For example, Table 1, which follows, contains a listing of voltages normalized to 1 volt that would be measured across the leads indicated as a function of the number and location of switches engaged. Note that in the preferred embodiment, the resistive elements 330 are resistors and the preferred normalized resistance of each is about 100 ohms, with the values in column C1 below being normalized to 1 volt.

By way of explanation, the column labeled "C1" contains resistances measured across contacts 315 and 320 with voltage applied to 310 and with 315 being grounded with swithes 410 through 470 closed as indicated. The values stored in the column labeled "C2" are the resistances measured across contacts 315 and 320 with voltage applied to 325 and with 315 being grounded with switches 410 through 470 closed as indicated. Finally, each cell that contains a bullet therein indicates that the corresponding switch 410 through 470 is closed.

Note that in some instances it is necessary to measure both circuits to uniquely determine the location and number of switches compressed. For example, the normalized voltage that would be observed when only switch 420 is closed (0.75, Row 2) is the same as would be observed if switches 410 through 450 were closed (0.75, Row 23). In such an instance, reference to the second circuit C2 (contacts 315 and 320) makes it possible to automatically differentiate between these two cases, as the C2 normalized voltages for these two conditions are 0.857 and 0.750 respectively.

Additionally, given the preferred arrangement of the instant invention, it is also readily possible to determine using the total number of switches/contacts that the patient's weight has closed. Those of ordinary skill in the art will recognize that the resistance between contacts 315 and 320 provides such a measure, preferably when used in concert with the "nearest switch" calculation developed above (circuit "C2", hereinafter). As a specific example, consider the case where the patient's weight has forced switches 440 and 450 into contact. The previous calculation has will have determined that at least switch 450 (the nearest) has been engaged. Given this information together with the results from Table 1, it is possible to determine how many contiguous switches have been closed by the patient's weight on the mat.

TABLE 1

Fractional Voltage Arising from Different Combinations of Closed Switches 410 to 470

| Row | 410 | 420 | 430 | 440 | 450 | 460 | 470 | C1 | Fraction | C2 | Fraction |
|---|---|---|---|---|---|---|---|---|---|---|---|
| 1 | • | | | | | | | 0.875 | 7/8 | 0.875 | 7/8 |
| 2 | | • | | | | | | 0.750 | 6/8 | 0.857 | 6/7 |
| 3 | | | • | | | | | 0.625 | 5/8 | 0.833 | 5/6 |
| 4 | | | | • | | | | 0.500 | 4/8 | 0.800 | 4/5 |
| 5 | | | | | • | | | 0.375 | 3/8 | 0.750 | 3/4 |
| 6 | | | | | | • | | 0.250 | 2/8 | 0.667 | 2/3 |
| 7 | | | | | | | • | 0.125 | 1/8 | 0.500 | 1/2 |
| 8 | • | • | | | | | | 0.857 | 6/7 | 0.857 | 6/7 |
| 9 | | • | • | | | | | 0.714 | 5/7 | 0.833 | 5/6 |
| 10 | | | • | • | | | | 0.571 | 4/7 | 0.800 | 4/5 |
| 11 | | | | • | • | | | 0.429 | 3/7 | 0.750 | 3/4 |
| 12 | | | | | • | • | | 0.286 | 2/7 | 0.667 | 2/3 |
| 13 | | | | | | • | • | 0.143 | 1/7 | 0.500 | 1/2 |
| 14 | • | • | • | | | | | 0.833 | 5/6 | 0.833 | 5/6 |
| 15 | | • | • | • | | | | 0.667 | 4/6 | 0.800 | 4/5 |
| 16 | | | • | • | • | | | 0.500 | 3/6 | 0.750 | 3/4 |
| 17 | | | | • | • | • | | 0.333 | 2/6 | 0.667 | 2/3 |
| 18 | | | | | • | • | • | 0.167 | 1/6 | 0.500 | 1/2 |
| 19 | • | • | • | • | | | | 0.800 | 4/5 | 0.800 | 4/5 |
| 20 | | • | • | • | • | | | 0.600 | 3/5 | 0.750 | 3/4 |
| 21 | | | • | • | • | • | | 0.400 | 2/5 | 0.667 | 2/3 |
| 22 | | | | • | • | • | • | 0.200 | 1/5 | 0.500 | 1/2 |
| 23 | • | • | • | • | • | | | 0.750 | 3/4 | 0.750 | 3/4 |
| 24 | | • | • | • | • | • | | 0.500 | 2/4 | 0.667 | 2/3 |
| 25 | | | • | • | • | • | • | 0.250 | 1/4 | 0.500 | 1/2 |
| 26 | • | • | • | • | • | • | | 0.667 | 2/3 | 0.667 | 2/3 |
| 27 | | • | • | • | • | • | • | 0.333 | 1/3 | 0.500 | 1/2 |
| 28 | • | • | • | • | • | • | • | 0.500 | 1/2 | 0.500 | 1/2 |

Of course, a principal reason for acquiring this information is so that it can be determined whether or not a patient has exhibited sufficient activity to skip the next scheduled assisted "turn". That is, in a typical arrangement a physician will prescribe that a patient be manually turned at some predetermined time interval, e.g., every two hours, so that the patient does not rest for too long a period of time in one position. As has been described previously, assisted turning is disruptive to the patient and taxing on the staff and, to the extent that the patient has already moved himself or herself, it may be that the next scheduled turn may and should be skipped.

However, those of ordinary skill in the art will recognize that not every movement by a patient is sufficient to reoxygenate the tissues that have been compressed by the patient's weight. For example, if a patient is resting on his or her right side and moves laterally across the bed without changing orientation, such a simple relocation would not relieve pressure from the compressed tissue and, as a consequence, the patient would likely still need to be manually turned.

Thus, it is preferred by the instant inventors that the location information which is obtained from the mat 300 be combined with logic (whether implemented by discrete logic, one or more gate arrays, analog circuitry, or via a CPU/software combination, etc.) to help determine whether or not the patient has moved significantly, where a significant move is one that persists at least long enough for there to be sufficient reoxygenation of the previously compressed tissues.

According to another preferred embodiment, there is provided an invention substantially as described above, but wherein the number of switch closures is determined by preferably applying a constant current to connector 320 while grounding either 310 or 315 and measuring the resulting voltage. Table 2 which follows illustrates how various switch closures will be reflected in the measured voltages.

TABLE 2

Fractional Current Arising from Different Combinations of Closed Switches 410 to 470

| Row | 410 | 420 | 430 | 440 | 450 | 460 | 470 | C3 Volts | C3* | C4 Volts | C4** |
|---|---|---|---|---|---|---|---|---|---|---|---|
| 1 | •*** |  |  |  |  |  |  | 2.9167 | 7 | 0.4167 | 1 |
| 2 |  | • |  |  |  |  |  | 2.5000 | 6 | 0.8333 | 2 |
| 3 |  |  | • |  |  |  |  | 2.0833 | 5 | 1.2500 | 3 |
| 4 |  |  |  | • |  |  |  | 1.667 | 4 | 1.667 | 4 |
| 5 |  |  |  |  | • |  |  | 1.2500 | 3 | 2.0833 | 5 |
| 6 |  |  |  |  |  | • |  | 0.8333 | 2 | 2.5000 | 6 |
| 7 |  |  |  |  |  |  | • | 0.4167 | 1 | 2.9167 | 7 |
| 8 | • | • |  |  |  |  |  | 2.5000 | 6 | 0.4167 | 1 |
| 9 |  | • | • |  |  |  |  | 2.0833 | 5 | 0.8333 | 2 |
| 10 |  |  | • | • |  |  |  | 1.667 | 4 | 1.2500 | 3 |
| 11 |  |  |  | • | • |  |  | 1.2500 | 3 | 1.667 | 4 |
| 12 |  |  |  |  | • | • |  | 0.8333 | 2 | 2.0833 | 5 |
| 13 |  |  |  |  |  | • | • | 0.4167 | 1 | 2.5000 | 6 |
| 14 | • |  | • | • |  |  |  | 2.0833 | 5 | 0.4167 | 1 |
| 15 |  | • | • | • |  |  |  | 1.667 | 4 | 0.8333 | 2 |
| 16 |  |  | • | • | • |  |  | 1.2500 | 3 | 1.2500 | 3 |
| 17 |  |  |  | • | • | • |  | 0.8333 | 2 | 1.667 | 4 |
| 18 |  |  |  |  | • | • | • | 0.4167 | 1 | 2.0833 | 5 |
| 19 | • |  | • | • | • |  |  | 1.667 | 4 | 0.4167 | 1 |
| 20 |  | • |  | • | • | • |  | 1.2500 | 3 | 0.8333 | 2 |
| 21 |  |  | • | • | • | • |  | 0.8333 | 2 | 1.2500 | 3 |
| 22 |  |  |  | • | • | • | • | 0.4167 | 1 | 1.667 | 4 |
| 23 | • |  | • | • | • | • |  | 1.2500 | 3 | 0.4167 | 1 |
| 24 |  | • |  | • | • | • | • | 0.8333 | 2 | 0.8333 | 2 |
| 25 |  |  | • | • | • | • | • | 0.4167 | 1 | 1.2500 | 3 |
| 26 | • |  | • | • | • | • | • | 0.8333 | 2 | 0.4167 | 1 |
| 27 |  | • | • | • | • | • | • | 0.4167 | 1 | 0.8333 | 2 |
| 28 | • | • | • | • | • | • | • | 0.4167 | 1 | 0.4167 | 1 |

By way of explanation, the values in the column headed by "C3 Volts" are the voltages read between 320 and 315 with a constant current, for example 4.167 mA, being applied to 320. Switches 410 through 470 are closed if a bullet is present in the corresponding column. The values stored in the column labeled "C4 Volts" are the voltages read between 320 and 310 with a constant voltage applied to 320, and with switches 410 through 470 being closed as indicated. If, for instance, each resistor 330 has been chosen to be 100 ohms, the voltage drop across each is 0.4167 volts. Thus, the number of resistors in the circuit may be calculated (assuming a given number of switch closures) and the results of such a calculation may be found in the columns in the Table 2 labeled C3 and C4. Note that each cell in the previous table that contains a bullet therein indicates that the corresponding switch 410 through 470 is taken to be closed. The values in the column headed by "C3" are the number of resistors read between 320 and 315 while a constant current is applied to 320 with switches 410 through 470 being closed as indicated. The values stored in the column labeled "C4" are the number of resistors read between 320 and 310 with a constant voltage being applied to 320 and with switches 410 through 470 being closed as indicated.

As should be clear in be reference to the previous table, by monitoring the measured voltage of the instant preferred sensor along two different paths, it is readily possible to determine which of the switches 410 through 470 are closed either individually or in combination. Note that the method of determining patient location with this embodiment is analogous to that discussed previously in the case where voltage application was utilized.

Figure 5:
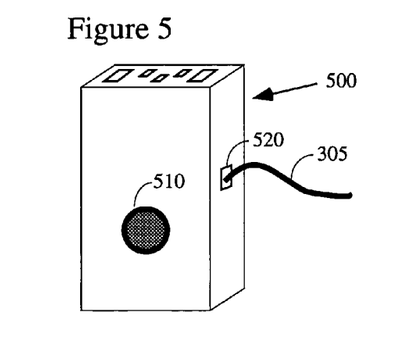
FIG. 5 contains an illustration of a preferred monitor for use with the instant invention.
Figure 6:
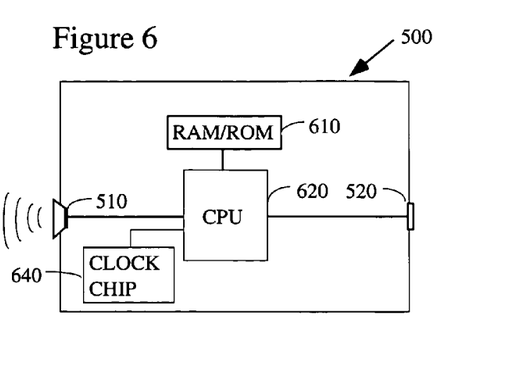
FIG. 6 is a schematic diagram of a preferred microprocessor-based electronic monitor for use with the instant inventive pressure sensitive mat.
Figure 11:
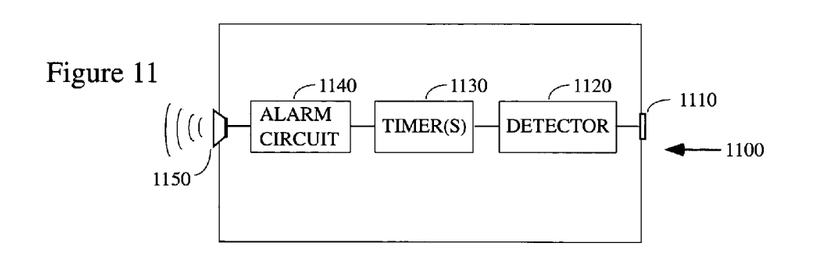
FIG. 11 contains a preferred electronic monitor embodiment, wherein no microprocessor is utilized.

In practice and as is generally illustrated in FIGS. 5, 6, and 11, the instant invention would be used as follows. As a first step, the sensor 300 would be placed into electronic communication with an electronic patient monitor 500. Typically, such a monitor 500 will contain an interface port 520 which preferably takes the form of a standard connector (e.g., an RJ-11-type connector) into which the sensor cord 305 is plugged. Within the monitor 500 will preferably be found a microprocessor 620 which might additionally utilize a separate timer/clock chip 640 to assist it in measuring the various time intervals that are useful and necessary in the monitoring of an at-risk patient. Of course, those of ordinary skill in the art will recognize that a separate (or external) clock chip 640 is not strictly necessary and, instead, software timing loops could readily be used instead. Finally, it is customary to include some amount of computer RAM/ROM 610 in which to store program instructions and variable values. That being said, those of ordinary skill in the art will recognize that such RAM/ROM 610 need not be external to the microprocessor 602 but might, instead, be incorporated into the microprocessor 602 according to methods well known to those of ordinary skill in the art.

Although the previous monitor embodiment 500 was microprocessor-based, those of ordinary skill in the art will recognize that the simple functionality that is minimally required of this monitor could readily be implemented with discrete logic components. As is generally suggested in FIG. 11, sensor port 1110 could be monitored by detector 1120 which might be comprised of, by way of example only, a position detection circuit, a window comparator, a sample-and-hold circuit, and a differential amplifier circuit. The detector circuit 1120 would preferably work in combination with one or more timers 1130, which timers would preferably include a timer for monitoring the doctor-prescribed turn interval (e.g., a two-hour timer) and a separate timer to determine whether the patient has maintained a changed position for a period of time sufficient to allow reoxygenation of the previously-compressed tissues (e.g., a ten-minute timer). Finally, if the alarm conditions are satisfied, an alarm circuit 1140 would be triggered which preferably would sound an audible alarm via speaker 1150 which might be directly incorporated into the patient monitor 1100 or situated remotely thereto, e.g., at a nurses station.

After the patient has been placed on the sensor 300 and the monitor 500 has been initialized, a determination of the patient's location and an estimate of his or her orientation will be made. The orientation will preferably be established by reference to the percentage of the mat 300 that is occluded. That is, if only a few (e.g., one or two) of the switches 410 through 470 are closed, the patient is likely lying on his or her side. However, if a larger number are closed (e.g., 3 or 4 or more), the patient is likely lying on his or her back or stomach. Of course, those of ordinary skill in the art will recognize that it is not the number of switches that are closed that is determinative of the patient orientation, but rather the proportion of the switches that are closed when compared with the total number of switches, such a proportion being a measure of the length of the contact area between the patient and the sensor 300.

Thereafter, the monitor 500 will continue to monitor the patient's location and orientation to determine whether or not the patient has moved. However, and as is well known to those of ordinary skill in the art, determining whether or not the patient has "moved" is not enough: the patient who is lying, say, on his right side and who moves sideways in the bed is still in risk of decubitus ulcers. Thus, by analyzing the location of the patient together with the number of switches engaged it will be possible to tell at least approximately whether the patient has truly moved to so that manual turning will not be necessary. For example, if the patient's weight has caused only two of the switches 410–460 to be engaged, that patient is likely lying on his or her side. However, if the weight distribution of the patient later changes to engage four of the switches 410–460, it is likely that the patient has rolled onto his or her back or stomach. Thus, the patient is unlikely to need to be manually turned.

In a typical arrangement, the patient will be monitored continuously by an attached electronic patient monitor during the time that he or she is bed-fast or chair-fast. Usually, the attending physician will prescribe a turn interval for the patient, the turn interval being the frequency with which the staff must manually turn the patient so that the compressed tissues can reoxygenate. A two-hour turn interval is commonly used. A preferred embodiment of the instant invention operates by determining an initial orientation of the patient on the sensor and then thereafter repeatedly redetermining the patient's position over time to ascertain whether or not he or she has moved. Those of ordinary skill in the art will understand that there is no set sampling frequency or period of time between measurements of the patient's position that need be used, but that the sampling interval must necessarily be shorter than the turn interval and, preferably, will be on the order of once a minute or so. Further, there is no requirement that the successive checks of the patient's position be equally spaced in time, although that is also preferred. Thus, when the period of time between successive patient measurements is alluded to herein, that time period should be understood to be shorter than the patient's turn interval and otherwise could be arbitrarily closely spaced in time.

Figure 7:
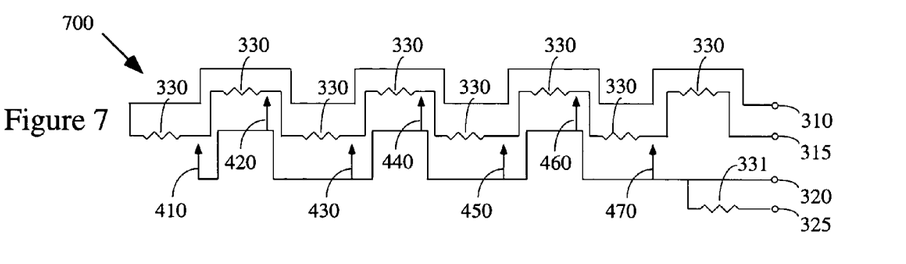
FIG. 7 illustrates another preferred embodiment of the instant invention, wherein the resistive ladder is configured so as to provide both a lateral and longitudinal patient position.

In another preferred embodiment of the instant invention, there is provided a sensor substantially as described above, but wherein a plurality of spaced-apart longitudinally aligned resistive ladders are utilized so as to give a horizontal and vertical profile of the patient's orientation in the bed, i.e., to provide both a longitudinal and vertical measurement of the patient's location. As is generally indicated in FIG. 7, in a preferred arrangement the resistive ladder of FIGS. 3 and 4 is spatially configured so as to give an approximate "X" and "Y" location of the patient on the sensor 700, where "X" is preferably measured with respect to the width of the bed and the "Y" with respect to its length. As is best illustrated in FIG. 7, by spatially varying the location of the resistive elements 330 and the switches 410–470, it is possible estimate, not only the lateral location of the patient on the mat, but also his or her vertical position relative to the head (or foot) of the bed. In more particular, consider the case where switches 440, and 460 are closed ("Case 1") in comparison with the case where, say, switches 450, and 470 are closed ("Case 2"). Generally speaking, the combination of switches in Case 1 would be interpreted as a patient who is higher (i.e., closer to the head) of the bed than the combination of Case 2. Thus, it should be clear that the preferred arrangement—which utilizes a series of staggered switches—can be used to obtain general information about the vertical location of the patient in the bed.

However, note that, in addition to giving an approximate "X" and "Y" position of the patient in the bed as has been discussed previously, the instant sensor 700 can provide dynamic/real-time information about the patient's condition by monitoring the changing closure patterns of its switches over time. For example, in the previous scenario where the closure pattern of Case 1 is followed directly by the pattern of Case 2, the patient is likely sliding toward the foot of the bed. Further, and in another preferred embodiment, this information will be utilized to estimate the amount of shear experienced by the patient's tissue during this time period.

Thus, in another preferred arrangement, there is provided a sensor and attached electronic patient monitor substantially as described above, but wherein the patient monitor utilizes information from the time-varying switch closures to help identify those patient's that are at risk of decubitus ulcers by virtue of shear stress placed on their tissues, a sheer stress being a force that is tangent to the skin's surface. As is well known to those of ordinary skill in the art, the amount of shear experienced by a patient is increasingly recognized as another factor in predicting the occurrence of decubitus ulcers. A patient's sliding down in the bed is an obvious source of such stress, and may, indeed, cut off oxygenated blood to the patient's tissues by capillary deformation, thereby increasing the risk of injury. If an at-risk patient can be automatically identified and the staff notified, additional manual intervention, or a change to another bed or chair, might circumvent the occurrence of ulcer formation entirely. Needless to say, it is much better to prevent decubitus ulcers than to treat them. Additionally, shear that is caused by sliding can indicate a general restlessness in the patient, which might be correlated with an increase in his or her pain or anxiety level. Those of ordinary skill in the art will recognize the utility of being able to automatically identify such a change in patient condition and to notify the staff so that intervention is possible if it is necessary.

Figure 8:
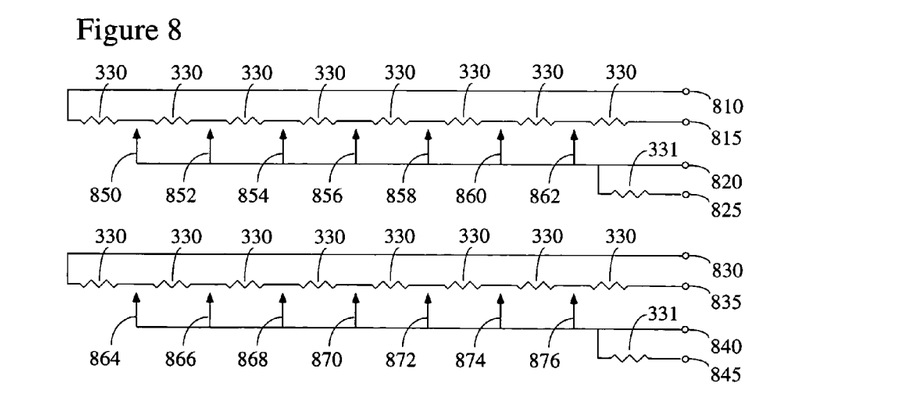
FIG. 8 contains a schematic illustration of another preferred embodiment of the instant invention, wherein the multiple resistive ladders are provided so as to provide both a lateral and longitudinal patient position.

According to another preferred embodiment, there is provided a mat substantially as described above, but wherein there are two or more resistive ladders configured in a roughly parallel arrangement. As is generally indicated in FIG. 8, in a preferred arrangement two or more electrically isolated resistive ladders are utilized, each such ladder being independently accessible via connectors 810 through 825 and 830 through 845, respectively. As should be clear by reference to this figure, switches 850 through 862 are separately readable to determine which are closed. These switches, in combination with switches 864 through 876 provide a horizontal, as well as a vertical, image of the patient's position. Given this sort of arrangement, it is possible to determine vertical and horizontal changes in the patient's position and, if desired, to estimate whether or not the patient's body is experiencing shear. As a specific example of how the presence of shear might be sensed, if the contract area (occluded region) of the mat remains constant, but the vertical (i.e., "Y") location of the patient indicates the he or she has moved down in the bed, the patient is likely being exposed to shear and the staff should be notified of this problem. Needless to say, there could be many more such parallel arrays of resistive elements than the two arrays that are illustrated in the embodiment of FIG. 8.

Figure 9:
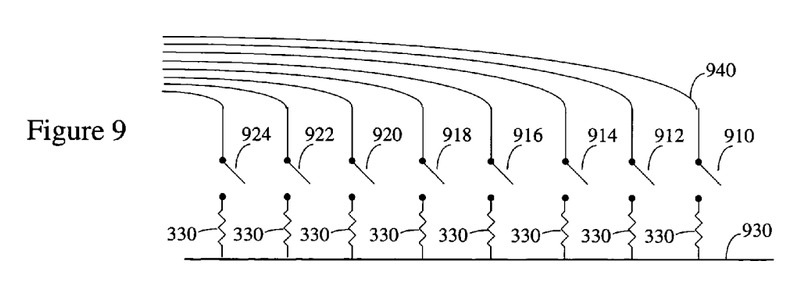
FIG. 9 contains a schematic illustration of another preferred embodiment of the instant invention, wherein each resistive element is separately readable.

According to still another preferred embodiment, there is provided a patient sensor substantially as described above, but wherein each resistive element is made part of a separate circuit that is individual readable by the microprocessor 620. That is, and as is generally indicated in FIG. 9, in a preferred arrangement each switch 910 through 924 is separately readable by virtue of the individual electrical lines coming to it. That is, rather than using a four-element electrical line 305, a nine-element line is preferably used instead, wherein each of the conductive elements leading to switches 910 through 924 is kept electrically isolated from the others. This means that a patient monitor in electrical communication with the embodiment of FIG. 9 can directly determine which of the switches is closed, e.g., by bringing each connecting line into a separate port in the microprocessor (or other programmable device) of the monitor. Note that in this case, the resistive elements 330 might take any resistive value that is greater than or equal to zero. Finally, note that although the switches in FIG. 9 and elsewhere in this disclosure are normally opened, those of ordinary skill in the art will recognize that normally closed switches could be used instead and that the procedure for determining patient location discussed previously would not need to modified materially in order to determine the patient's position.

Additionally, it should be noted in connection with FIGS. 4 and 9 that it would be readily possible to create switches that are based on optical, rather than electrical, properties, wherein the resistive element takes the form of an optical attenuator. That is, if the electrical conductor 930 were instead replaced by some sort of optical fiber, if resistive elements 330 included sections of optical fiber, and, if, for example, the amplitude or frequency of light passing through the switch were changed (e.g., attenuated or amplified) when the patient were present on the sensor, closure of the switches 910–924 could be determined by, for example, monitoring the amplitude of light received through lead 940.

Figure 12:
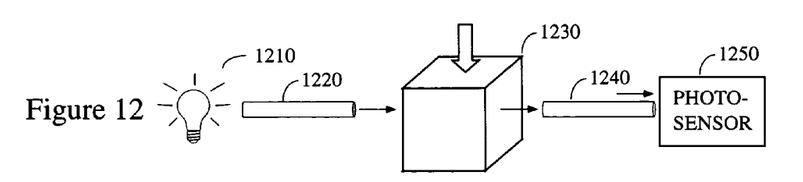
FIG. 12 contains an optical switch embodiment suitable for use with the instant invention, wherein a foam block or similar material is used as an optical attenuator.

FIG. 12 illustrates a first preferred optical switch that would be suitable for use with an optical embodiment of the instant invention. In this embodiment a block of open cell foam or similar material acts as the optical attenuator. By way of explanation, a light source 1210 is provided at one end of an optical conduit 1220 (e.g., a section of fiber optic cable). Light is transmitted through the optically conductive material 1220 until it reaches optical attenuator 1230, which in one preferred embodiment is a low density open cell foam. A portion of the light that falls on the attenuator 1230 will be transmitted therethrough to optical conduit 1240 (e.g., a section of fiber optic cable) where it will be further conducted to photo-sensor 1250. As is well know to those of ordinary skill in the art, when open cell foam is compressed (e.g., via the weight of the patient on the sensor) its density increases and it becomes less transparent to light. Thus, by measuring the intensity of light that is received at photo-sensor 1250 it will be possible to determine whether or not the foam block is compressed and, hence, which of the switches within the sensor are "closed". In a preferred arrangement, an initially calibrated amount of light that is transmitted through the attenuator 1230 when the foam is not compressed will be continuously compared with the actual amount of light received from light source 1210.

Figure 13A:
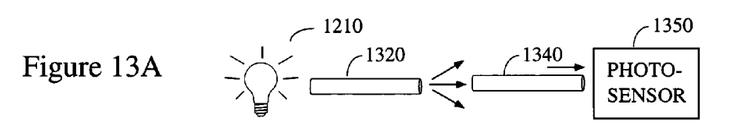
FIG. 13 contains another preferred optical switch embodiment wherein misalignment of two optical fibers is used as an optical attenuator.
Figure 13B:
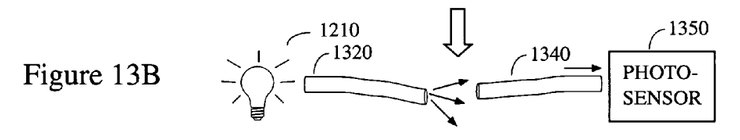

According to a second preferred optical switch embodiment, and as is generally illustrated in FIGS. 13A and 13B, there is provided an optical attenuator which utilizes misalignment of two optical conduits as a means of attenuating the optical signal when the patient is present on the sensor. When the patient is not present on the sensor (FIG. 13A) the ends of optical conduits 1320 and 1340 will be in near direct alignment and much of the light that emanates from the source conduit 1320 will be received by receiver conduit 1340, depending, of course, on the distance between the two conduits. The patient's weight on the sensor, which is typically made to be at least somewhat flexible for purposes of the increasing the patient's comfort, would tend to misalign the two optical conduits (FIG. 13B) and reduce the amount of light transmitted between them. A photo-sensor 1250 in optical communication with the receiving conduit 1340 would thus be readily able to determine whether or not the switch was engaged depending on the level of light received. Preferably, a reference level of light transmissivity will be established while the mat is empty so that deviations therefrom can be identified. The optical attenuation in this case is brought about by the degree of physical misalignment between the sections of optical conduit. Preferably a calibration value will be provided against which the currently measured optical intensity will be measured which will then provide an indication of when the termini of the two conduits 1320 and 1340 are in alignment. Pressure on the sensor (which is typically made to be at least somewhat flexible for purposes of increasing the patient's comfort) will force the two conduits into at least partial misalignment, thereby reducing the amount of light transmitted therebetween (FIG. 13B). Thus, by monitoring the quantity of light received through a plurality of such optical switches it is possible to determine the patient's position location on the sensor and the amount of the sensor that is occluded which is, of course, correlated with the patient's orientation.

Figure 14:
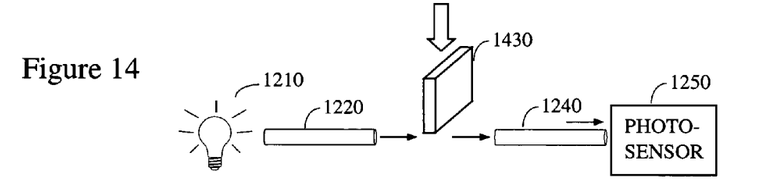
FIG. 14 contains still another preferred optical switch embodiment which utilizes a movable plate or similar structure to block passing between two sections of optical fiber, thereby attenuating the amount of light passing therebetween.

In still another preferred optical switch embodiment and as is generally indicated in FIG. 14, there is provided an optical switch suitable for use with the instant invention, wherein a shutter 1430 moves downward under the pressure of the patient's weight to block the transmission of light between source conduit 1220 and receiver conduit 1240. Clearly, placing a photo sensor 1250 in optical communication with receiver conduit 1240 would make it possible to determine whether or not the subject switch were open and, hence, whether the patient were present on the sensor.

Figure 15:
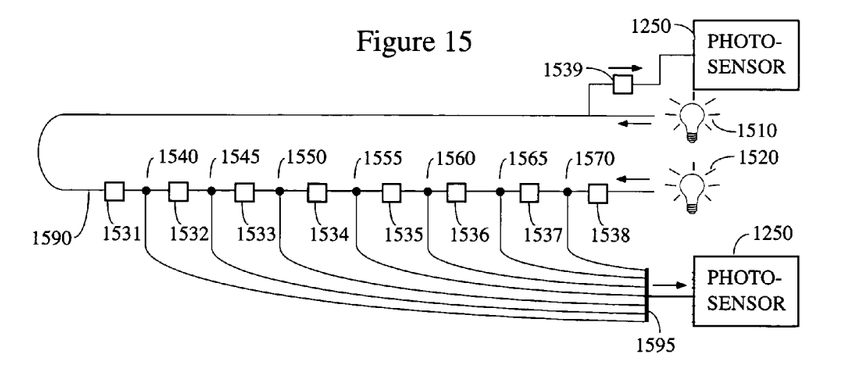
FIG. 15 illustrates a preferred sensor embodiment, wherein optical switches and attenuators are used instead of electrical resistors.

As a final example of an optical embodiment of the instant invention, there is provided in FIG. 15 a preferred arrangement wherein a plurality of optical attenuators 1530 (e.g., any of the attenuators of FIGS. 12 to 14, but the embodiment of FIG. 14 would likely be best suited) are placed in series with light collectors 1540–1570 interspersed in between. Preferably and for purposes of the instant embodiment, the light originating from all of the light collectors 1540–1570 will be additively combined through junction 1595 into a single optical conduit where it can be read by photo-sensor 1250. For purposes of illustration only, the attenuators will be assumed to be the shutters 1430 of FIG. 14. According to one preferred embodiment, light sources 1510 and 1520 will be positioned at opposite ends of the light conduit 1590 and alternately activated. That is, light source 1510 will be activated while source 1520 is dark, and then light source 1510 will be darkened while source 1520 is activated. The reason for this arrangement is that it allows a patient's location and occlusion to be readily determined using a single photo-sensor 1250. If, for example, optical attenuators 1532–1535 are engaged (i.e., the shutters of these optical attenuators are in the "down" or blocking position) light from source 1510 will be received only at collector 1540, with the remaining collectors 1545–1570 being dark. However, when optical source 1520 is activated, light will be received at collectors 1560 through 1570, with the remaining collectors being dark (i.e., 1540 through 1555) being dark. Given this information, it is possible to determine the number of switches open (or engaged) on the left and on the right and, thus, the position and amount of occlusion of the sensor by the patient. Note that in many ways the operation of the optical embodiment of FIG. 15 is analogous to the operation of the electrical embodiment of FIG. 4. Finally, note that, if desired a calibration optical attenuator 1539 could added so that, by reading the amount of light transmitted therethrough and comparing the observed value with the presumably known nominal value for this element, a correction factor could be established that could be applied to the other attenuators 1531–1538.

Note that if a microprocessor is utilized as a component of the monitor 500, the only requirement that such a component must satisfy is that it must minimally be an active device, i.e., one that is programmable in some sense, that it is capable of recognizing signals from a bed mat or similar patient sensing device, and that it is capable of initiating the sounding of one or more alarm sounds in response thereto. Of course, these sorts of modest requirements may be satisfied by any number of programmable logic devices ("PLD") including, without limitation, gate arrays, FPGA's (i.e., field programmable gate arrays), CPLD's (i.e., complex PLD's), EPLD's (i.e., erasable PLD's), SPLD's (i.e., simple PLD's), PAL's (programmable array logic), FPLA's (i.e., field programmable logic array), FPLS (i.e., fuse programmable logic sequencers), GAL (i.e., generic array logic), PLA (i.e., programmable logic array), FPAA (i.e., field programmable analog array), PsoC (i.e., programmable system-on-chip), SoC (i.e., system-on-chip), CsoC (i.e., configurable system-on-chip), ASIC (i.e., application specific integrated chip), etc., as those acronyms and their associated devices are known and used in the art. Further, those of ordinary skill in the art will recognize that many of these sorts of devices contain microprocessors integral thereto. Thus, for purposes of the instant disclosure the terms "processor," "microprocessor" and "CPU" (i.e., central processing unit) should be interpreted to take the broadest possible meaning herein, and such meaning is intended to include any PLD or other programmable device of the general sort described above.

Additionally, in those embodiments taught herein that utilize a clock or timer or similar timing circuitry, those of ordinary skill in the art will understand that such functionality might be provided through the use of a separate dedicate clock circuit or implemented in software within the microprocessor. It might further be obtained with discrete, linear, timers and logic circuitry: a microprocessor is not strictly required, but is merely convenient. Thus, when "clock" or "time circuit" is used herein, it should be used in its broadest sense to include both software and hardware timer implementations.

Figure 10:
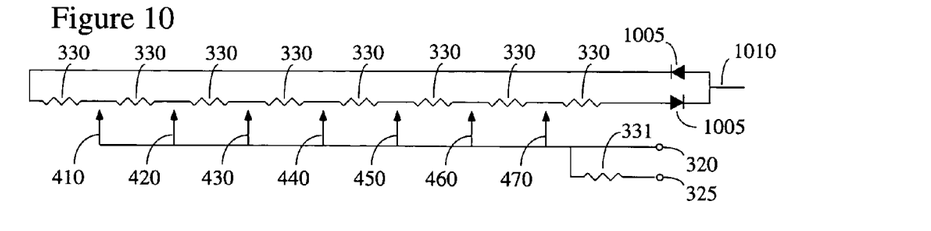
FIG. 10 illustrates another preferred embodiment, wherein the number of interconnect electrical conduits has been reduced by one.

Finally, and according to still another preferred embodiment, there is provided a patient sensor substantially similar to that disclosed previously, but wherein the number of connecting electrical leads has been reduced. As is illustrated generally in FIG. 10, those of ordinary skill in the art will recognize that by using diodes 1005 it is possible to eliminate connectors 310 and 315 and replace them with a single electrical lead 1010. That being said, it should be noted that, in reality, the number of connectors has not been reduced but rather only the number of interconnects. As a consequence, for purposes of the instant disclosure and the claims that follow, when it is noted that three conductors are required, that language should not be limited to those cases where three discrete interconnects are utilized, but rather should be understood in the broader sense to mean any configuration of conductors and connectors that is adequate to allow an attached electronic patient monitor to determine the number of switch closures when a patient is present on the sensor.

Conclusions

Although the preferred embodiment of the instant invention utilizes a ladder of electrical resistors to determine the position of the patient on the sensor, it should be clear to those of ordinary skill in the art that capacitive or inductive elements, some combination of same, semiconductors (e.g., forward biased diodes or zener diodes), temperature sensors (e.g., thermocouples), piezoelectric elements, etc. could readily be used instead. Of course, rather than measuring the resistance across leads 310 through 325 it would be possible to measure the resonance time constant (RC or LC time constant) or some other quantity representative of the number of circuits that are closed in the mat. In fact, the instant invention could also be configured to operate by calculating the various travel times of an electronic pulse that is sent through the instant circuitry (e.g., as measured by a Ditmico tester). Note that, in the preferred embodiment, the resistive elements 330 are preferably created by screening additional lengths of the electrically conductive material onto the mat surface, thereby creating increased resistance. This additional length would also result in an increased travel time as well, so a technique that measured the travel time of an electronic pulse from, say, 320 to 310 and from 315 to 320 would be able to determine the number of switches closed by the patient's weight. Thus, as used herein, when the term "resistive value" is used to describe the measurement of some electrical property of the circuit, it should be understood that the quantity that is actually measured might be different from "resistance" and, instead, could be any other property that is representative of the number of switches that are closed in the attached mat including, without limitation, capacitance, voltage, transit time, etc. Similarly, when reference is made herein to electrical properties, electrical conductors, and electrical resistors that same language should be understood to also include optical properties, optical conductors, and optical attenuators.

Additionally, although the preferred arrangement includes an array of identical resistive elements, those of ordinary skill in the art will recognize that this arrangement is not required. It is certainly possible that some combination of different-valued resistive elements (e.g., different resistor values) might be used and, in such a circumstance, methods similar to those discussed herein could be used to determine exactly which switches are closed when a patient is present on the device.

Those of ordinary skill in the art will recognize that the preferred embodiment, with its plurality of switches, could easily be manufactured with any number of separate switches. At the limit, of course, these switches when spaced closely together begin to approximate a continuum of contact points. Thus, it should be noted and remembered that the instant inventors have determined that the invention taught herein might be implemented in substantially the same way in the form of a single continuous resistive element. In such an embodiment, preferably the single continuous resistive element will be used with a plurality discretely spaced activation (e.g., switches 410 through 460), the goal being to determine the nearest point of contact of the patient to one end of the mat and the occluded/contact area.

Further, note that the instant invention may be utilized to detect when a patient is moving toward the edge of the sensor with the intent of exiting the bed. It should be clear that if none of the mat switches are engaged, the patient is no longer present on the mat and, presumably, will have left the bed or chair into which he or she had been placed. Thus, the instant invention can function in connection with a conventional "exit monitor" and be used to signal the nursing staff when a patient has risen. This much should be clear. However, note that, because the preferred mat embodiment has numerous switches distributed along its length, it is possible to utilize the instant invention determine when a patient is preparing to leave the bed and, if so desired, signal that intent to the nursing staff. Note that the preferred embodiment has switches distributed throughout the length of the mat, including switches that are proximate to each end. Typically, when a patient is intending to leave the bed, his or her weight is relocated laterally to the exit side as a prelude to exiting. Further, the speed with which the patient moves toward the edge of the bed may also be telling, with faster movements toward the bed edge usually being indicative of a patient that is preparing to exit the bed. Through the use of the instant invention, it is possible to determine when the patient's weight so-shifts by looking for instances when only the switches proximate to one end of the mat are engaged. Additionally, the velocity at which the patient moves toward the edge may also be calculated. In the event that the patient approaches the edge of the bed and/or approaches the edge of the bed in excess of a predetermined velocity, a signal will preferably be sent to the nursing staff, thereby allowing the staff to intervene before the patient has had time to stand and fall.

Additionally, although it is preferred that the instant sensor be placed under the patient's hips or back, that is not the only possible orientation. Of some additional concern is the condition of the patient's heels, elbows, and other bony prominences. Each of these sites can potentially be a site at which decubitus ulcers can develop. Although the sensor of the instant invention could certainly be positioned under any of these areas and/or multiple sensors could be used (e.g., one under each area of concern), more practically speaking the those of ordinary skill in the art will recognize that monitoring the patient's movement at his or her hips allows at least some general inferences about the other locations of concern (e.g., if the patient has rolled on his or her side it is likely that the heels are in a position to reoxygenate, etc.)

Further, it should be noted and remembered that, although a preferred embodiment of the instant invention employs a discrete central spacer, that is not absolutely required. That is, it is certainly possible that the role of the "spacer" could be filled by a series of noncontiguous nonconductive "dots" or other discrete shapes that have been imprinted across the conductive elements 380 (e.g. the support elements 390). Thus, for purposes of the instant invention, the terms "spacer" and "central spacer" should be broadly interpreted to include any structure that serves to separate the upper 350 and lower 360 members of the instant invention when there is no weight on the mat 300. Similarly, when the central spacer is described as having "apertures", it should be recognized that these might take the form of the embodiment of FIG. 3 (i.e., holes formed within an otherwise solid central member) or they might take them form of spaces between adjacent support members (e.g., non-conductive dots), etc. In any case, a principle function of the "apertures" is to allow the upper 350 and lower 360 members to come into contact when pressure is applied to the mat and, thus, any sort of structure that permits or facilitates that operation should be considered to be an "aperture" for purposes herein.

Additionally, although it is preferable that the resistive elements 330 be screened onto the inner face of the mat 300 and thus be integrated with the mat, it should be clear that separate discrete electronic components could readily be used instead. For example, discrete resistors could be affixed to the mat 300 to serve in place of screened-on resistive elements 330. Those of ordinary skill in the art will recognize that such an arrangement—provided that some provision were to be made so that the resistors could not be felt through the mat 300 by the patient—would function identically to the preferred embodiment discussed above.

Note further that a preferred electronic monitor of the instant invention utilizes a microprocessor with programming instructions stored therein for execution thereby, which programming instructions define the monitor's response to the patient. Although ROM is the preferred apparatus for storing such instructions, static or dynamic RAM, flash RAM, EPROM, PROM, EEPROM, or any similar volatile or nonvolatile computer memory could be used. Further, it is not absolutely essential that the software be permanently resident within the monitor, although that is certainly preferred. It is possible that the operating software could be stored, by way of example, on a floppy disk, a magnetic disk, a magnetic tape, a magneto-optical disk, an optical disk, a CD-ROM, flash RAM card, a ROM card, a DVD disk, or loaded into the monitor over a network as needed. Additionally, those of ordinary skill in the art will recognize that the memory might be either internal to the microprocessor, or external to it, or some combination. Thus, "program memory" as that term is used herein should be interpreted in its broadest sense to include the variations listed above, as well as other variations that are well known to those of ordinary skill in the art.

Additionally, although the preferred embodiment of the instant invention utilizes a plurality of resistive elements 330 organized in a serial arrangement, alternative circuit configurations (e.g., parallel, or some other arrangement) could certainly be employed instead. All that is required for purposes of the instant invention is that the mat circuit, whatever its configuration, be capable of determining at least an occluded/contact region and a location from one end of the mat. Of course, a sensor which yielded a distance from each end of the mat would allow an immediate calculation of the occluded or contact region. Those of ordinary skill in the art will be able to devise many alternative configurations of the instant invention beyond those suggested herein.

Further, it should be noted and remembered that, although the preferred embodiment of the instant invention has the two circuits 323 and 335 and the resistive elements 330 and 331 all physically located on the same surface of mat 300, it should be clear that various permutations of this arrangement are possible. Indeed, the only requirement is that the resistive elements 330 be in electrical communication with the circuits 323 and 325 so that the sensor 300 functions as has been described previously. Thus, it would be within the spirit of the instant invention if the resistive elements 330 were to be located, say, on the central spacer 355 or on the inner face of mat surface 360. Similarly, the two circuits 323 and 335 need not be physically resident on the same mat element 350, but could instead be on opposite mat elements so long as they can be selectively closed to indicate at least a patient's approximate lateral location as a function of the number of switches closed. Additionally, those of ordinary skill in the art will recognize that it is certainly possible that the sensor 300 might be made a part of, or incorporated, into the bed itself or some other structure.

Finally, it should be noted that the term "nurse call" as that term has been used herein should be interpreted to mean, not only traditional wire-based nurse call units, but more also any system for notifying a remote caregiver of the state of a patient, whether that system is wire-based or wireless (e.g., R.F., ultrasonic, IR link, etc.). Additionally, it should be clear to those of ordinary skill in the art that it may or may not be a "nurse" that monitors a patient remotely and, as such, nurse should be broadly interpreted to include any sort of caregiver, including, for example, untrained family members and friends that might be signaled by such a system.

Thus, it is apparent that there has been provided, in accordance with the invention, a patient sensor and method of operation of the sensor that fully satisfies the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. A patient sensor for use in monitoring a patient who is at risk of developing decubitus ulcers, said patient sensor having at least a first end and a second end, comprising:
   (a) a nonconductive upper member, said upper member having an outer surface and an inner surface,
      wherein at least a portion of said upper member inner surface is electrically conductive;
   (b) a nonconductive lower member, said lower member having an inner surface and an outer surface, said lower member inner surface being positionable to be proximate to said upper member inner surface,
      wherein at least a portion of said lower member inner surface is electrically conductive, said electrically conductive portion of said lower member inner surface containing at least two electrically isolated circuits thereon,
         (b1) wherein a first circuit of said at least two electrically isolated circuits contains at least a plurality of spaced apart resistive elements therein, and,
         (b2) wherein a second circuit of said at least two electrically isolated circuits, when taken in combination with said first circuit, forms a plurality of switches, each of said switches having at least one of said resistive elements associated therewith and each of said switches being located at a predetermined distance from said first end of said patient sensor;
   (c) a nonconductive central spacer between said upper member and said lower member, said central spacer
      electrically separating at least a portion of said upper member and said lower member inner surfaces, and,
      allowing at least a portion of said conductive portions of said upper member and said lower member to come into electrical contact when a patient is present on said patient sensor, thereby electrically engaging at least one of said plurality of switches and the resistive elements associated therewith; and,
   (d) an electrical line in electrical communication with said conductive portions of said upper and lower members, said electrical line having at least three electrically isolated conductors therein, wherein
      (d1) a first conductor of said at least three conductors is in electrical communication with said first circuit,
      (d2) a second conductor of said at least three conductors is in electrical communication with said first circuit, such that by measuring the potential between said first and second conductors a total resistance in said first circuit may be determined, and
      (d3) a third conductor of said at least three conductors is in electrical communication with said second electrically isolated circuit, such that by measuring a total resistance between said first circuit and said second circuit a determination may be made of a location and extent of said at least one point of contact.

2. A patient sensor according to claim 1, further comprising:
   (e) an electronic patient monitor in electrical communication with said patient sensor via said electrical line, said patient monitor at least for determining the patient's position on the sensor and an amount of the patient sensor occluded by the patient.

3. A patient sensor according to claim 2, wherein said electronic patient monitor comprises at least:
(e1) a CPU, said CPU being positionable to be in electronic communication with said electrical line and with said first and second circuits,
(e2) a time circuit in electrical communication with said CPU,
(e3) a speaker in electrical communication with said CPU, said speaker being operable under control of said CPU to generate an alarm in response thereto,
(e4) computer memory, said memory in electrical communication with said CPU and at least containing a plurality of computer instructions executable by said CPU, said computer instructions comprising at least the steps of:
(1) determining a first resistive value across said first and second conductors,
(2) determining a second resistive value across said first and third conductors,
(3) determining from said first and second resistive values at least an initial nearest engaged resistive element of said plurality of resistive elements, wherein said nearest engaged resistive element is measured with respect to said first end,
(4) determining from said first and said second resistive values an initial number of said resistive elements that are engaged,
(5) after a period of time has elapsed, determining a third resistive value across said first and second conductors, and, determining a fourth resistive value across said first and said third conductors,
(6) determining from said third and said fourth resistive values a current nearest engaged resistive element of said plurality of resistive elements, wherein said current nearest engaged resistive element is measured within respect to said first end,
(7) determining from said first and second resistive values a current number of said resistive elements that are engaged,
(8) using at least said initial nearest contact point, said current nearest contact point, said initial number of resistive elements that are engaged, and said current number of resistive elements that are engaged to determine whether the patient has moved during a predetermined period of time,
(9) if the patient has moved during said period of time, performing steps (1) through (8) as necessary to reduce the risk of decubitus ulcers in the patient, and,
(10) if the patient has not moved during said period of time, sounding an alarm at least through said speaker to indicate that the patient has not moved, thereby reducing the risk of decubitus ulcers in the patient.

4. A patient sensor for use in monitoring a patient according to claim 3, wherein said first, second, third, and fourth resistive values are resistances.

5. A patient sensor for use in monitoring a patient according to claim 3, wherein said resistive elements are capacitors and said first, second, third, and fourth resistive values are capacitances.

6. A patient sensor for use in monitoring a patient according to claim 1, wherein said resistive elements are resistors.

7. A patient sensor for use in monitoring a patient according to claim 1, wherein said resistive elements are resistors all having a same resistance.

8. A patient sensor for use in monitoring a patient according to claim 1 wherein said first circuit contains a plurality of linearly spaced apart resistive elements connected together serially.

9. A patient sensor for use in monitoring a patient according to claim 1 wherein said first circuit contains a plurality of linearly spaced apart resistive elements connected together in parallel.

10. A patient sensor for use in monitoring a patient according to claim 1 wherein each of said resistive elements is a thermocouple.

11. A patient sensor for use in monitoring a patient who is at risk of developing decubitus ulcers, said patient sensor having at least a length and a first end and a second end, comprising:
(a) a nonconductive lower member, said lower member having an inner surface and an outer surface,
wherein said lower member inner surface has at least one resistive ladder thereon, said at least one resistive ladder having a plurality of serially connected spaced apart resistive elements spanning at least a portion of said length of said patient sensor, and,
wherein said nonconductive lower member inner surface has an electrically isolated contact circuit proximate to said resistive ladder;
(b) a nonconductive upper member, said upper member having an outer surface and an inner surface,
wherein at least a portion of said upper member inner surface is electrically conductive,
(c) a nonconductive central spacer positionable to be between said upper member and said lower member, said central spacer
separating said electrically conductive portions of said upper member and said lower member, and,
allowing said electrically conductive portions of said upper member and said lower member to come into contact when pressure is applied to said patient sensor, thereby electrically shorting said first circuit and said second circuit at a point of contact when said contact is made; and,
(d) an electrical line in electrical communication with said conductive portions of said upper and lower members, said electrical line having at least three electrically isolated conductors therein, wherein
(d1) a first conductor of said at least three conductors is in electrical communication with said first circuit,
(d2) a second conductor of said at least three conductors is in electrical communication with said first circuit such that by measuring the potential between said first and second conductors a total amount of resistance in said first conductor may be determined, and
(d3) a third conductor of said at least three conductors is in electrical communication with said second electrically isolated circuit.

12. A patient sensor for use in monitoring a patient according to claim 11, wherein said resistive elements are resistors.

13. A patient sensor for use in monitoring a patient according to claim 11, wherein said resistive elements are resistors having a same resistance.

14. A method of monitoring a patient who is at risk of developing decubitus ulcers,
wherein is provided
a patient sensor positionable to be proximate to the patient and being operable to provide at least a proportion of the sensor occluded by the patient and a contact point of the patient on the sensor, and, a patient turn interval, comprising the steps of:

(a) determining whether a patient is present on the sensor;

(b) using said patient sensor to determine an initial contact point of the patient on the sensor;

(c) using said patient sensor to determine an initial occluded region of the patient on the sensor;

(d) waiting a period of time;

(e) using said patient sensor to determine a subsequent contact point of the patient on the sensor;

(f) using said patient sensor to determine a subsequent occluded region of the patient on the sensor;

(g) using at least said initial contact point, said initial occluded region, said subsequent contact point, and said subsequent occluded region to determine whether the patient has moved during said period of time;

(h) if the patient has not moved during said period of time, determining a time since the patient last moved;

(i) if said time since the patient last moved exceeds said patient turn interval, sounding an alarm;

(j) if said time since the patient last moved does not exceed said patient turn interval, continuing to perform steps (d) through (i) until either the patient moves again or until the time since the patient last moved exceeds said patient turn; and, (k) if the patient has moved during said time period, continuing to perform steps (d) through (j) until either the patient moves again or until the patient turn interval is exceeded.

15. A method of monitoring a patient who is at risk of developing decubitus ulcers according to claim 14, wherein is said patient sensor contains at least one resistive ladder therein, said at least one resistive ladder being operable to provide at least a proportion of the sensor occluded by the patient and a contact point of the patient on the sensor.

16. A patient sensor for use in monitoring a patient who is at risk of developing decubitus ulcers, comprising:

(a) a nonconductive upper member, said upper member having an outer surface and an inner surface, at least a portion of said upper member inner surface being electrically conductive;

(b) a nonconductive lower member, said lower member having an inner surface and an outer surface, said lower member inner surface being positionable to be proximate to said upper member inner surface, said upper member and said lower member together defining an interior region of said patient sensor when so positioned, (c) a first electrical circuit within said interior region of said patient sensor, said first circuit comprising a plurality of spaced apart resistive elements, (d) a second electrical circuit within said interior region of said patient sensor, wherein, (d1) said second electrical circuit is electrically isolated from said first electrical circuit, and, (d2) said conductive portion of said upper member inner surface causes said second electrical circuit to electrically engage said first electrical circuit when said patient sensor is compressed, (e) a nonconductive central spacer positionable between said upper member and said lower member, said central spacer electrically separating said upper member and said lower member when so positioned, and, allowing said second circuit to engage said first circuit when pressure is applied to said patient sensor, thereby electrically shorting said first circuit and said second circuit at at least one point of contact; and, (f) an electrical line having at least three electrically isolated conductors therein, wherein (f1) a first conductor of said at least three conductors is in electrical communication with said first circuit, (f2) a second conductor of said at least three conductors is in electrical communication with said first circuit such that by measuring the potential between said first and second conductors a total amount of resistance in said first conductor may be determined, and (f3) a third conductor of said at least three conductors is in electrical communication with said second electrically isolated circuit.

17. A patient sensor for use in monitoring a patient according to claim 16, wherein said resistive elements are resistors.

18. A patient sensor for use in monitoring a patient according to claim 16, wherein said resistive elements are selected from a group consisting of capacitors, diodes, or inductors.

19. A patient sensor for use in monitoring a patient according to claim 16 wherein said first circuit contains a plurality of linearly spaced apart resistive elements connected together serially.

20. A patient sensor for use in monitoring a patient according to claim 16 wherein said first circuit contains a plurality of linearly spaced apart resistive elements connected together in parallel.

21. A patient sensor for use in monitoring a patient according to claim 16, wherein said electrical line has at least four electrical connectors, and further comprising:

(g) a third electrical circuit within said interior region of said patient sensor, said third electrical circuit (g1) comprising a plurality of spaced apart resistive elements, (g2) being electrically isolated from said first electrical circuit and said second electrical circuit, and, (g3) being in electrical communication with said fourth electrical lead, (g4) wherein said conductive portion of said upper member inner surface causes said second electrical circuit to electrically engage said first electrical circuit, or said third electrical circuit, or both when said patient sensor is compressed.

22. A patient sensor for use in monitoring a patient who is at risk of developing decubitus ulcers, wherein said sensor is configured to be positioned beneath the patient, comprising:

(a) a nonconducting upper member, said upper member having a perimeter and an inner surface;

(b) a nonconducting lower member, said lower member having a perimeter and an inner surface, and said lower member being sized to be at least approximately commensurate with said upper member, said upper and lower members being joined together along their perimeters, said upper and lower members taken together forming an interior of said patient sensor therebetween;

(c) a nonconducting central spacer, positioned between said upper and lower members and separating at least a portion of upper member inner surface from contact with said lower member inner surface;

(d) a first conductor within said interior of said patient sensor, said first conductor having a first end and a second end, and said first conductor comprising at least a plurality of serially interconnected resistive elements;
(e) a plurality of spaced apart serially connected switches, wherein
(e1) each of said switches engages said first conductor at a predetermined location when activated,
(e2) at least a portion of each of said switches is located on said upper member inner surface and another portion of each of said switches is located on said lower member inner surface, and,
(e3) each of said switches can be separately activated by the patient when said sensor is positioned underneath the patient, each switch being so activated only when it is at least approximately directly beneath the patient; and,
(f) a second conductor in electrical communication with said serially connected switches, said second conductor coming into electrical communication with said first conductor if at least one of said switches is activated in response to a patient's presence on said sensor, whereby
(f1) measuring an electrical property between said second conductor and said first end of said first conductor provides a value representative of an activated switch nearest said first end of said first conductor, and,
(f2) measuring an electrical property between said second conductor and said second end of said first conductor provides a value representative of an activated switch nearest said second end of said first conductor.

23. A method according to claim 22, wherein said resistive elements are resistors and said measured electrical properties between said first conductor and said second conductor are resistances.

24. A method according to claim 22, wherein said resistive elements are capacitors and said measured electrical properties between said first conductor and said second conductor are capacitances.

25. A patient sensor for use in monitoring a patient according to claim 23, wherein said resistive elements are thermocouples and said measured electrical properties between said first conductor and said second conductor are voltages.

26. A patient sensor for use in monitoring a patient according to claim 22, wherein said resistive elements are resistors all having a same resistance.

27. A patient sensor for use in monitoring a patient according to claim 22, further comprising:
(g) a calibration resistive element in electrical communication with said second conductor, said calibration resistive element having a nominal resistive value and being separately measurable to determine an actual resistive value, said actual resistive value at least for use in scaling said first circuit resistive elements.

28. A patient sensor for use in monitoring a patient according to claim 22, further comprising:
(g) an electronic patient monitor in electronic communication with said sensor, said electronic patient monitor at least for
(g1) determining a position of the patient on the sensor and an amount of said sensor occluded by the patient,
(g2) determining a time since the patient last moved, and,
(g3) generating an alarm signal at least if said time since the patient last moved exceeds a predetermined time value.

29. A patient sensor for use in monitoring a patient who is at risk of developing decubitus ulcers, said sensor at least for providing a patient's position and an amount of said sensor occluded by the patient's presence thereon, said patient sensor being positionable to be placed beneath the patient, comprising:
(a) a nonconductive upper member, said upper member having an outer surface and an inner surface,
(b) a nonconductive lower member, said lower member having an inner surface and an outer surface, said lower member inner surface being positionable to be proximate to said upper member inner surface, said upper member and lower member together forming an interior of said sensor,
wherein at least a portion of said lower member inner surface is electrically conductive, said electrically conductive portion of said lower member inner surface comprising at least a plurality of resistive elements connected in parallel by at least one conductor, said plurality of resistive elements and said at least one conductor comprising a resistive circuit;
(c) a plurality of spaced apart switches within said interior of said sensor,
(c1) wherein each of said switches is positioned at a predetermined location within the sensor,
(c2) wherein at least a portion of each switch is on said upper member inner surface;
(c3) wherein at least a portion of said switches engage a matching number of said resistive elements when the sensor is positioned beneath the patient, and,
(c4) wherein each of said plurality of switches is separately readable to determine which of said switches is engaged, thereby providing information related to said position of the patient and said amount of said sensor occluded by the patient; and,
(c) a nonconductive central spacer between said upper member and said lower member, said central spacer
electrically separating at least a portion of said upper member and said lower member inner surfaces when said sensor is not beneath the patient, and,
allowing at least a portion of said conductive portions of said upper member and said lower member to come into electrical contact when a patient is present on said patient sensor, thereby electrically engaging at least one of said plurality of switches and the resistive elements associated therewith, and,
(d) a plurality of electrical lines in electrical communication with said plurality of switches, wherein,
(d1) each of said electrical lines is electrically isolated from the other,
(d2) each of said electrical lines is in electrical communication with a different one of said plurality of switches, and,
(d2) measuring an electrical property between any of said electrical lines and said resistive circuit provides a signal indicative of whether said associated switch is engaged.

30. A method according to claim 29, wherein said resistive elements are resistors and said measured electrical property between any of said electrical lines and said resistive circuit is a resistance.

31. A patient sensor for use in monitoring a patient according to claim 30, wherein said resistive elements are resistors all having a same resistance.

32. A method according to claim 29, wherein said resistive elements are capacitors and said measured electrical property between any of said electrical lines and said resistive circuit is a capacitance.

33. A patient sensor for use in monitoring a patient according to claim 29, wherein said resistive elements are thermocouples and said measured electrical property between any of said electrical lines and said resistive circuit is a voltage.

34. A patient sensor for use in monitoring a patient according to claim 29, further comprising:
    (e) an electronic patient monitor in electrical communication with said patient sensor and with said plurality of electrical, said electronic patient monitor at least for determining an approximate location of the patient from any switch engagements.

35. A patient sensor for use in monitoring a patient according to claim 34, wherein said electronic patient monitor contains a microprocessor therein, said microprocessor programmed to perform the steps of at least determining an approximate location of the patient from any switch engagements.

36. A method of calibrating patient sensor, said patient sensor at least for use in sensing an amount of said sensor occluded by a patient and said patient sensor at least containing a resistive ladder therein, said resistive ladder being comprised of at least two resistive elements, each of said at least two resistive elements having a nominal resistive value associated therewith, and wherein is further provided a calibration resistive element within said patient sensor, said calibration resistive element having a nominal resistive value representative of said resistive values of said at least two resistive elements, said method comprising the steps of:
    (a) measuring a total resistance of all of said at least two resistive elements;
    (b) measuring a resistance of said calibration resistive element;
    (c) adjusting said measured total resistance based on said measured resistance of said calibration resistive element;
    (d) using at least said adjusted measured total resistance to determine an amount of said sensor occluded by the patient.

37. A method of calibrating a resistive ladder according to claim 36, wherein each of said at least two resistive elements and said calibration resistive element have a same nominal resistance.

38. A method of calibrating a resistive ladder according to claim 37, wherein step (c) comprises the step of:
    (c1) dividing said measured total resistance by said measured resistance of said calibration resistive element, thereby adjusting said measured total resistance.

39. A patient sensor for use in monitoring a patient, said sensor at least for providing a patient's position and an amount of said sensor occluded by the patient's presence thereon, said patient sensor being positionable to be placed beneath the patient, said patient sensor having an interior, comprising:
    (a) a resistive ladder within said patient sensor, said resistive ladder containing a plurality of resistive elements therein, each of said resistive elements having a nominal resistive value associated therewith;
    (b) a plurality of switches, each of said switches engaging one of said resistive elements when said switch is placed beneath the patient, each of said switches being located at a predetermined location within said sensor interior; and,
    (c) first, second, and third leads in communication with said resistive ladder, whereby,
        (c1) said first and second leads taken together provide a signal at least representative of a distance of the patient from an end of said sensor, and,
        (c2) said first and third leads taken together provide a signal at least representative of an amount of said sensor occluded by the patient's presence thereon.

40. A patient sensor according to claim 39, wherein said first, second, and third leads are electrical leads and said resistive elements are selected from a group consisting of consisting of electrical resistors, capacitors, diodes, or inductors.

41. A patient sensor according to claim 39, wherein said first, second, and third leads are fiber optic leads and said resistive elements are optical attenuators.

42. A patient sensor according to claim 39, further comprising:
    (d) a calibration resistive element in communication with said resistive ladder, said calibration resistive element having a nominal resistive value representative of said nominal resistive values of said resistive elements in said resistive ladder.

43. A patient sensor according to claim 39, further comprising:
    (d) an electronic patient monitor in communication with said patient sensor, said electronic patient monitor at least for reading said plurality of signals and determining therefrom said patient position and said amount of said sensor occluded by the patient.

44. A patient sensor according to claim 39, wherein each of said nominal resistive values of said resistive elements is a same value.

* * * * *